Figure 6:
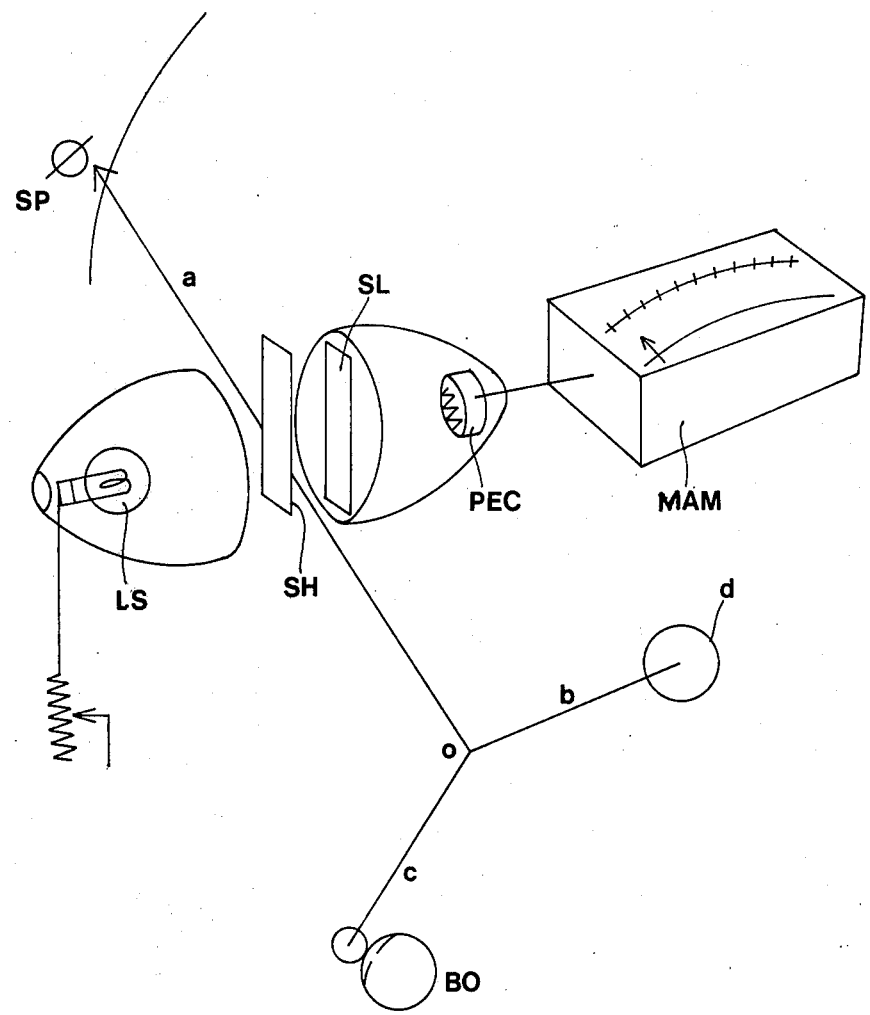

United States Patent [19]

Foddis

[11] 4,064,743

[45] Dec. 27, 1977

[54] UNIVERSAL EYE PRESSURE IMPULSE TONOMETER AND METHOD OF MEASURING THE INTRA-OCULAR PRESSURE

[76] Inventor: Antonio Foddis, Viale A. Diaz (Grattacielo p.1), 29, Cagliari, Italy

[21] Appl. No.: 699,276

[22] Filed: June 24, 1976

[51] Int. Cl.² .............................................. A61B 9/00
[52] U.S. Cl. ........................................ 73/80; 128/2 T
[58] Field of Search ............................ 73/80; 128/2 T

[56] References Cited

U.S. PATENT DOCUMENTS

| 3,308,653 | 3/1967 | Roth | 73/80 |
|---|---|---|---|
| 3,613,666 | 10/1971 | Hobbs | 73/80 X |

Primary Examiner—Jerry W. Myracle
Attorney, Agent, or Firm—Cullen, Settle, Sloman & Cantor

[57] ABSTRACT

A tonometer and method of measuring the intra-ocular pressure, comprising a three armed structure including a horizontal arm to which a weight can be applied and second and third arms extending obliquely upwardly and downwardly from the end of the horizontal arm, said third arm supporting a measuring body applicable to the eyeball to exert pressure thereon by the action of said weight to increase the intra-ocular pressure so that when said weight is suddenly removed said released increased pressure will cause the three-armed structure to oscillate and these oscillations are measured.

8 Claims, 6 Drawing Figures

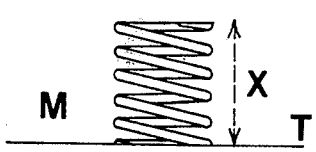
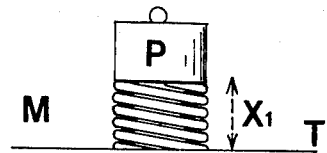
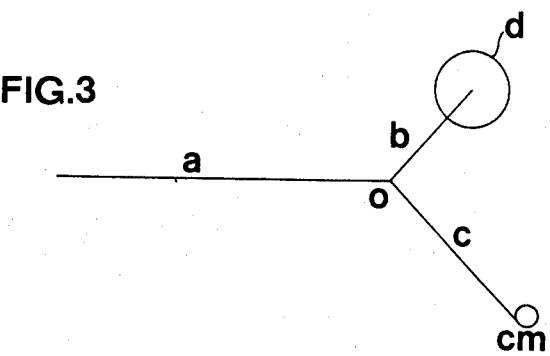
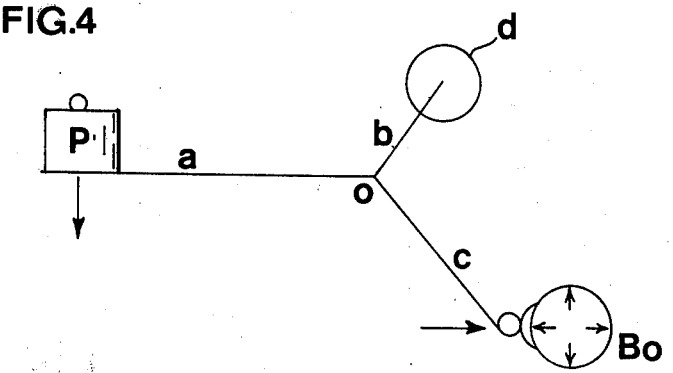
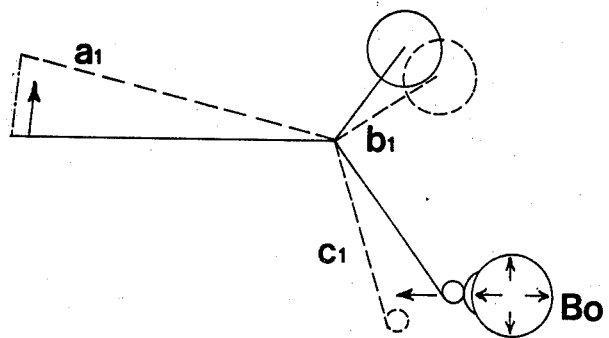

UNIVERSAL EYE PRESSURE IMPULSE TONOMETER AND METHOD OF MEASURING THE INTRA-OCULAR PRESSURE

This invention relates to a universal eye pressure impulse tonometer and method for measuring the intraocular pressure by measuring the impulse produced when a pressure exerted on the eyeball is suddenly released.

For numerous clinical examinations necessary in ophthalmology it is of primary importance to ascertain the intra-ocular pressure which can be safely established only by introducing a pressure gauge cannula into the eye. As this involves a risky surgical operation it is only used to calibrate the conventional tonometers which indirectly permit to ascertain the approximate value of the intra-ocular pressure although they are liable to numerous errors.

The principle of operation of all eye tonometers used today is based on an analysis of the deformation of the cornea when it is subjected to the action of a weight while a status of equilibrium is established between the eye and the weight. Irrespective of whether the examination is concerned with a corneal indentation (Schötz tonometer) or corneal aplanation (Goldmann tonometer) the readings obtained merely represent physical indications of static conditions.

Present tonometry is not only liable to errors caused by the necessity to use indirect systems, but is also limited in practice because it is directed to the analysis of a deformation which necessitates that the morphology of the cornea (the place within the eye where the deformation is to be produced) should not be too distant from an ideal condition which however often is not provided by nature or is upset by previous pathological processes.

Clinical practice has taught that the corneal curvature in the area of vision, which is the area involved by tonometrical examinations, on an average comprises an area of about three millimeters in diameter around the center of the corneal apex, the radius of curvature being often different from one patient to another and even between the eyes of the same patient. Astigmatism, even if it is perfectly regular, does not permit the production of a completely circular aplanatic area. Also cases of irregular astigmatism such as in patients afflicted by keratoconus and keratitis or the consequences thereof, or having cicatrices resulting from operations or perforating wounds and the like, do not permit to ascertain the exact intro-ocular pressure.

Thus it can be said that there is no tonometric system that may be considered suitable for universal use in clinical practice. This leads to two fundamental considerations:

The operation of the conventional tonometers is based on measurements of a corneal deformation which cannot always be correctly interpreted.

The operation of the conventional tonometers is based on a principle of what in physics are called static phenomena.

Experience has shown that when a weight acts on the eyeball not only a deformation of the cornea is produced but other phenomena in the interior of the eyeball. In fact, the deformation of the cornea causes a displacement of the aqueous humor from its seat, resulting in an increase of the pressure in the eyeball. With the same weight acting on the cornea the deformed surface area is the greater the smaller is the actual intra-ocular pressure. The same applies to the volume of the displaced aqueous humor which also causes a corresponding increase of the intra-ocular pressure.

Thus, the three described phenomena, i.e. the deformation of the cornea, the amount of displaced aqueous humor and the increase of the effective intra-ocular pressure, must be regarded as concomitant and interdependent factors and their behavior is determined by the same mathematic law of proportionality. To establish the amount of deformation of the cornea (by conventional or modern tonometry) or ascertain the quantity of displaced aqueous humor or measure the value of the pressure increase produced by the effect of a predetermined weight acting on the eyeball are three indirect systems which must be considered equivalent as to the results obtained thereby. So all the previous systems were based upon an interpretation of the deformation of the cornea which, as explained above, is dependent on corneal morphology.

It is an object of the present invention to provide a universally applicable method and tonometer which eliminates the potential errors of the known methods. This is achieved according to the invention in that unlike what happens in the known methods which examine the deformation of the cornea, variations of introocular pressure are ascertained by directly examining the phenomena within the eyeball whose real values are to be established.

Other objects, features and advantages of the invention will become apparent from the following detailed description of a preferred embodiment with reference to the accompanying drawings in which:

FIGS. 1 and 2 are schematic views illustrating the behavior of the cornea, when a weight is applied thereto, with reference to a spring which behaves in the same manner, FIGS. 3 and 5 are schematic views illustrating the manner of operation of the tonometer proposed according to the present invention, and FIG. 6 is a schematic view illustrating the use of the tonometer in connection with a photoelectric system for detecting its oscillations.

Referring first to FIGS. 1 and 2, a status of stable equilibrium in a system of forces will be explained with particular reference to what happens in the absence of the action of only one of these forces. M represents a spring having a length X and a predetermined strength $r$. The spring M is firmly secured to the ground T (FIG. 1). A weight P of a predetermined value, for example 10 grams, is then applied to the spring M, as shown in FIG. 2. The weight P causes a compression or deformation of the spring M resulting in a reduction of its length $X > X_1$, which can be measured, and the spring assumes a potential elastic power corresponding to the potential power of gravitation lost by the weight P.

Now if the behavior of the spring as a result of the force applied thereto and its deformation is to be determined, its strength must be measured. This can be done in two ways. The first way is the direct way of measuring the deformation produced by the application of the weight P, this being the known way. The second way is the indirect way which consists in calculating the impulse delivered by the spring to an appropriately small, known mass, assuming that before the delivery of this impulse the spring possesses a certain potential elastic power which is a function of its strength and determined by the known size of the weight P. In practice the spring can be compressed until it is in a state of equilibrium with the weight P, can be locked in this state, then the weight P can be replaced by a weight $p$ smaller than P, and then the spring can be released. The described operation can be compared with the loading of the spring of a rifle and its subsequent release when the rifle is fired.

The behavior of the human eye is substantially the same as that of the mechanical model described above. As mentioned before, a weight P of a predetermined size, applied to the eye, not only produces a deformation of the cornea but also an increase of the intra-ocular pressure above its effective value. As in the physical model discussed above, the system of the eye plus the weight P will after a short time acquire a new state of stable equilibrium and a new potential power which is a function of the intra-ocular pressure and capable of producing an impulse that can be measured by the measuring instrument or tonometer proposed by the present invention.

The operation of this instrument is schematically illustrated in FIGS. 2 to 5. It serves to determine the value of the impulse produced as described above and so ascertain the value of the intra-ocular pressure which is indicated by Bo in FIGS. 4 and 5. The instrument essentially comprises a three-armed mechanical system formed of three equally spaced rigid metal arms $a$, $b$ and $c$. These arms are rotatable about the axis $o$ where they are rigidly connected. The arm $a$ normally assumes a horizontal position and has a free end adapted to receive a weight P. The arm $b$ in the normal position of the instrument extends obliquely upwardly away from the point of connection $o$ with the arm $a$ and may rotatably carry at its free end a balance roller $d$ of an appropriately soft material such as rubber so that it may serve as a cushioning pad to be applied to the forehead of the patient for positioning the instrument on the eye. With the use of the balance roller $d$ the length of the arm $a$ may be made greater than that of the arm $b$ to conveniently accommodate the weight P at the free end of the arm $a$. At any rate the weight of the arm $a$ must be equal to that of the arm $b$ and to achieve this, preferably the balance roller $d$ is used rather than making the two arms of equal length. With the two arms of equal length without a balance weight on the arm $b$ the instrument would be more difficult to apply to the patient's eye and also would be less sensitive to oscillations about the axis $o$, which is essential to the present invention as will be explained hereafter.

A third arm $c$ is rigidly connected to the axis $o$ and extends obliquely downwardly therefrom and away from the arm $a$ in the normal horizontal position of the latter. The arm $c$ carries a measuring body $cm$ at its free end, this measuring body being adapted to be applied to the patient's eye. The weight of the arm $c$ must be greater than that of the arm $a$ and that of the arm $b$.

The mechanical behavior of this three-armed structure will be similar to that of a flywheel. In fact, the structure may rotate about the axis $o$ until rotation is stopped by natural friction and the structure will assume a position of stable equilibrium. This position of stable equilibrium will only be achieved after a considerable amount of rotation and oscillation and will be constantly maintained only if one of the three arms (the arm $c$ in FIGS. 3 and 4) will be given a weight slightly greater than that of the other arms. The system is so designed that this position of stable equilibrium will occur when the arm $a$ is in a completely horizontal position.

Now when the measuring body $cm$ (FIG. 3) at the free end of the arm $c$ is brought into contact with the eyeball Bo, as shown in FIG. 4, and a weight P of predetermined size (10 or 5 grams) is applied to the free end of the arm $a$, the action of the weight P will be transmitted to the eyeball in the direction of the arrows shown in FIG. 4 and the effect of this action will be the same for each individual examination provided that the arm $a$ is previously brought into a completely horizontal position (calibration of the instrument).

The effect of the weight P on the eyeball will produce within the eyeball a certain potential power which will be transmitted to the measuring body $cm$ and from the measuring body to the entire mechanical three-armed system in the form of an impulse when the action of the weight is suddenly interrupted by removing the weight P. This impulse will be proportional to the potential power accumulated within the eyeball as a function of the internal pressure therein and will produce more or less wide oscillations of the three-armed mechanical system, as indicated by the arrows and dash lines in FIG. 5. FIG. 5 shows how the arms $a$, $b$, and $c$ immediately after removing the weight P will occupy the respective dash line positions $a_1$, $b_1$ and $c_1$ and will then for a certain time continue to oscillate between the dash line and full line positions.

These oscillations can then be measured with respect to their amplitude and duration, preferably at the free end of the arm $a$, for example, by a photoelectric system.

Such a system is shown in FIG. 6 and comprises a light source LS, a photoelectric cell PEC and a maximum milliamperemeter MAM. The light source LS is arranged on one side of arm $a$ of the tonometer and the photoelectric cell PEC is located on the other side thereof and connected to the milliamperemeter MAM. The photoelectric cell PEC is arranged in a suitable housing provided at its end adjacent the arm $a$ of the tonometer with an elongated slot SL. In a position adjacent the slot SL, a shutter SH of substantially the same shape and size of the slot is secured to the arm $a$ of the tonometer.

It will thus be seen that as the arm $a$ oscillates, the shutter SH oscillating with the arm $a$ will intermittently partially close the slot SL and will produce corresponding oscillations in the intensity of light detected by the photoelectric cell PEC and in the intensity of current produced by the photoelectric cell and transmitted to and indicated by the maximum milliamperemeter MAM which is capable of indicating the current intensities up to a maximum intensity corresponding to a maximum extent of oscillation of the tonometer arm $a$. The starting or zero position of the tonometer arm $a$ is indicated by SP.

A photoelectric system would have the advantage over other detecting means that it would also permit to establish the exact moment in which the arm $a$ is in a completely horizontal position and the weight P must be immediately removed. Obviously when the weight P is removed the balance roller $d$ should not be in contact with the patient's forehead to allow oscillation of the three-armed structure about the axis of rotation $o$. To ensure free oscillation of the three-armed structure it may also be turned round so that the balance roller $d$ will be directed downwardly.

If the same experiment is repeated with two different weights (of 10 and 5 grams, respectively) on the same eye, it is also possible to ascertain the values of the scleral strength.

Although a preferred embodiment of the invention has thus been described with reference to the accompanying drawings, it is to be understood that the invention is not limited to this precise embodiment and that numerous changes and modifications may be made therein within the scope of the appended claims. For example, the material used for the arms, their structural form and practical construction, except as herein specified, can be selected as desired. It is also obvious to one skilled in the art that to avoid manual holding of the instrument, the axis $o$ may be formed by a shaft rotatably supported at its ends in a supporting structure adapted to rest on the patient's head and carrying also the oscillation detection means.

I claim:

1. A universal eye pressure impulse tonometer comprising a three-armed structure including a first arm generally horizontal in the normal operative position of the tonometer and adapted to receive a weight at a free end, a second arm rigidly connected to the other end of said first arm and extending obliquely upwardly therefrom, said first and second arms being of equal weight, and a third arm rigidly connected to said other end of said first arm and extending obliquely downwardly therefrom, said third arm having a weight greater than each of said first and second arms and carrying at its free end a measuring body adapted to be brought into engagement with an eyeball, said weight exerting a pressure through said three-armed structure and said measuring body on the eyeball to produce an increase of the intra-ocular pressure, said weight being removable so that the increased intra-ocular pressure thus released will cause oscillation of the three-armed structure about an axis of oscillation formed by the point of connection between said three arms, said oscillations being measurable by detecting means, aligned with and opposed to a portion of said first arm and responsive to its oscillations towards and away from said detecting means.

2. A universal eye pressure impulse tonometer as claimed in claim 1, wherein said detecting means are photoelectric detecting means arranged adjacent the free end of said first arm.

3. A universal eye pressure impulse tonometer as claimed in claim 1, wherein said second arm is shorter than said first arm and rotatably carries at its free end a balance roller to compensate the greater weight of said first arm.

4. A universal eye pressure impulse tonometer as claimed in claim 3, wherein said balance roller consists of an appropriately soft material such as rubber and can be brought into engagement with a patient's forehead to position said measuring body on the patient's eyeball.

5. A universal eye pressure impulse tonometer as claimed in claim 3, wherein said three-armed structure can be rotated through 180° about an axis formed by said first arm so that said balance roller is located downwardly of said measuring body and said weight is also applicable to the opposite side of said first arm and measurements can be taken with the three-armed structure thus rotated.

6. A method of measuring the intra-ocular pressure, comprising the steps of placing a three-armed structure with a first arm in a horizontal position and a second and third arm extending respectively upwardly and downwardly from one end of said first arm, said second and third arms being rigidly connected to said first arm, bringing a measuring body on the free end of said third arm into engagement with the eyeball, applying a weight to said first arm to exert a pressure on the eyeball through said three-armed structure and said measuring body, said pressure producing an increase of the intra-ocular pressure, suddenly removing the weight from said first arm whereby said increased intra-ocular pressure will cause oscillation of said three-armed structure about an axis of oscillation formed by the point of connection between said three arms, and measuring the amplitude and duration of said oscillations.

7. A method of measuring the intra-ocular pressure as claimed in claim 6, wherein said oscillations are measured in the vicinity of the free end of said first arm.

8. A method of measuring the intra-ocular pressure as claimed in claim 6, wherein said oscillations are measured by photoelectric oscillation detecting means.

* * * * *